United States Patent [19]
Elliott et al.

[11] Patent Number: 5,883,266
[45] Date of Patent: Mar. 16, 1999

[54] HYDROGENATED 5-CARBON COMPOUND AND METHOD OF MAKING

[75] Inventors: Douglas C. Elliott; John G. Frye, both of Richland, Wash.

[73] Assignee: Battelle Memorial Institute, Richland, Wash.

[21] Appl. No.: 8,356

[22] Filed: Jan. 16, 1998

[51] Int. Cl.$^6$ ...................... C07D 309/00; C07D 307/02; C07C 27/00

[52] U.S. Cl. .................. 549/273; 549/508; 549/429; 568/864

[58] Field of Search .................................. 549/273, 429, 549/508; 568/864

[56] References Cited

U.S. PATENT DOCUMENTS

| | | | |
|---|---|---|---|
| 2,368,366 | 1/1945 | Kyrides et al. | 260/344 |
| 2,809,203 | 10/1957 | Leonard | 260/343.6 |
| 4,550,185 | 10/1985 | Mabry | 549/508 |
| 4,609,636 | 9/1986 | Mabry et al. | 502/183 |
| 4,782,167 | 11/1988 | Rao | 549/326 |
| 4,973,717 | 11/1990 | Williams | 549/508 |
| 4,985,572 | 1/1991 | Kitson et al. | 549/326 |
| 5,149,680 | 9/1992 | Kitson et al. | 502/185 |

FOREIGN PATENT DOCUMENTS

WO 92/02298  2/1992  WIPO.

OTHER PUBLICATIONS

Kitano, M., Tanimoto, F., Okabayashi, M. "Levulinic Acid, A New Chemical Raw Material —Its Chemistry and Use," *Chem. Econ. Eng. Rev.* 7(7) 25–29, 1975.

Leonard, R.H. "Levulinic Acid as a Basic Chemical Raw Material," *Ind. & Eng. Chem.* 48(8) 1331–1341, 1956.

Thomas, J.J., Barile, R.G. "Conversion of Cellulose Hydrolysis Products to Fuels and Chemical Feedstocks," in *Energy from Biomass and Wastes VIII*, pp. 1461–1494, Institute of Gas Technology, Chicago, Illinois, 1984.

Christian, R.V., Jr., Brown, H.D., Hixon, R.M. "Derivatives of γ–Valerolactone, 1,4–Pentanediol, and 1,4–Di–(–cyanoethoxy)–pentene," *Jour. Amer. Chem. Soc.* 69, 1961–1963, 1947.

Freer, Perkin, "The Synthetical Formation of Closed Carbon–Chains," *Jour. Chem. Soc.* 51, 836–837, 1887; Lipp, A. About 1,4–Pentanediol and Its Anhydride (Methyltetrahydrofuran), *Chemische Berichte* 22, 2567–2573, 1889.

Olah, G.A.; Fung, A.P.; Malhotra, R, "Synthetic Methods and Reactions; 99. Preparation of Cyclic Ethers over Superacidic Perfluorinated Resinsulfonic Acid (Nafion–H) Catalyst," *Synthesis*, 474–476, 1981.

Smith, K.; Beauvais, R.; Holman, R.W. "Selectivity versus Reactivity: The Safe Efficient Metal Hydride Reduction of a Bifunctional Organic," *Jour. Chem. Educ.* 70(4) A94–A95, 1993.

Schutte, H.A.; Sah, P.P.T.; "Norman Valerolactone," *Jour. Amer. Chem. Soc.* 48, 3163–3165, 1926.

Allen, B.B.; Wyatt, B.W.; Henze, H.R. "The Catalytic Hydrogenation of Some Organic Acids in Alkaline Solution," *Jour. Amer. Chem. Soc.* 61, 843–846, 1939.

Cook, P.L. "The Reduction of Aldehydes and Ketones with Nickel–Aluminum Alloy in Aqueous Alkaline Solution," *Jour. Org. Chem.* 27, 3873–3875, 1962.

Schutte, H.A.; Thomas, R.W. "Normal Valerolactone. III. Its Preparation by the Catalytic Reduction of Levulinic Acid with Hydrogen in the Presence of Platinum Oxide," *Jour. Amer. Chem. Soc.* 52, 3010–3012, 1930.

Jacobs, W.A.; Scott, A.B. "The Hydrogenation of Unsaturated Lactones to Desoxy Acids,", 601–613, 1930.

Broadbent, H.S.; Campbell, G.C.; Bartley, W.J.; Johnson, J.H. "Rhenium and Its Compounds as Hydrogenation Catalysts. III. Rhenium Heptoxide," *Jour. Org. Chem.* 24, 1847–1854, 1959.

Broadbent, H.S.; Selin, T.G. "Rhenium Catalysts. VI. Rhenium (IV) Oxide Hydrate," *Jour. Org. Chem.* 28(9) 2343–2345, 1963.

Folkers, K.; Adkins, H. "The Catalytic Hydrogenation of Esters to Alcohols. II," *Jour. Amer. Chem. Soc.* 54, 1145–1154, 1932.

Joó, Tóth, Z.; Beck, M.T. "Homogeneous Hydrogenation in Aqueous Solutions Catalyzed by Transition Metal Phosphine Complexes,"*Inorg. Chim. Acta* 25, L61–62, 1977.

Joó, F.;Somsák, L.; Beck M.T. "Peculiar Kinetics of Hydrogenations Catalyzed by Chlorotris–(sulphonated Triphenylphosphine) rhodium (I) in Aqueous Solutions," *Jour. Mole. Catal.* 24, 71–75, 1984.

Bracca, G.; Raspolli–Galletti, A.M.; Sbrana, G. "Anionic Ruthenium Iodocarbonyl Complexes as Selective Dehydroxylation Catalysts in Aqueous Solution," *Jour. Organomet. Chem.* 417, 41–49, 1991.

Osakada, K.; Ikariya, T.; Yoshikawa, A. "Preparation and Properties of Hydride Triphenylphosphine Ruthenium Complexes with 3–Formyl(or Acyl) Propionate," *Jour. Organomet. Chem.* 231, 79–90, 1982.

*Primary Examiner*—Amelia Owens
*Attorney, Agent, or Firm*—Paul W. Zimmerman

[57] ABSTRACT

The present invention is based upon the surprising discovery that a 5-carbon compound selected from the group of 4-oxopentanoic acid, at least one lactone of 4-oxopentanoic acid, and combinations thereof, may be hydrogenated with a bimetallic catalyst of a noble metal in combination with a second metal and preserve the pendant methyl group. It was further unexpectedly discovered that the same conditions of bimetallic catalyst in the presence of hydrogen are useful for catalyzing the different intermediate reactions for example angelicalactone to gamma-valerolactone and gamma-valerolactone to 1,4-pentanediol. Finally, it was surprising that levulinic acid could be converted to 2-methyltetrahydrofuran with heating in the presence of the bimetallic catalyst and hydrogen in a single process vessel. The method of the present invention unexpectedly produced a fuel or fuel component having 2-methyltetrahydrofuran either in a yield greater than 4.5 mol % or in combination with alcohols.

36 Claims, 6 Drawing Sheets

HYDROGENATED 5-CARBON COMPOUND AND METHOD OF MAKING

This invention was made with Government support under Contract DE-AC06 76RLO 1830 awarded by the U.S. Department of Energy. The Government has certain rights in the invention.

FIELD OF THE INVENTION

The present invention relates generally to a hydrogenated 5-carbon compound, and a method of making it, or more specifically a composition having at least 25 mol % 2-methyltetrahydrofuran and method of making 2-methyltetrahydrofuran from a five-carbon organic compound. The compound 2-methyltetrahydrofuran is denoted herein as MTHF.

BACKGROUND OF THE INVENTION

Levulinic acid is a well-known product of hexose acid hydrolysis [1,2], it being formed in a 72/28 ratio with formic acid. Numerous attempts have been made of the past century to commercially produce levulinic acid, but its utilization on a large scale has never been accomplished. All current production is apparently limited to small operations in Europe and Japanese production was reported as recently as 1975. Developers in Florida [3] in the 1980s used levulinic acid derivatives, both 2-methyltetrahydrofuran (MTHF) and angelicalactone, as fuel blending agents, which is supported by single engine test stand data. Accordingly, levulinic acid conversion to MTHF is useful as a fuel or fuel additive. In addition, it may be useful for making polymer fibers.

Because levulinic acid may be inexpensively obtained from cellulose, for example pulp waste and/or agricultural waste, there is motivation to find an economic way of converting the levulinic acid to MTHF.

Direct production of MTHF from levulinic acid is not reported in the literature except as a minor byproduct [4]. Copper-chromium oxide was used to catalyze the hydrogenation in a two stage manner at 245° C. and 300° C. and required about 80 minutes. The reaction yielded 11% gamma-valerolactone and 44% 1,4-pentanediol with a 22% yield of a water byproduct with the "odor of a alpha-methyl tetrahydrofuran", but no quantitative analysis of the water byproduct was reported, (estimated 4.5 mol % yield of MTHF in the water byproduct).

However, there has been extensive reporting of processing of levulinic acid and its derivatives which eventually leads to MTHF production. There are two pathways of interest, first beginning with a dehydration step via angelicalactone, and the second beginning with hydrogenation of the levulinic acid to the 4-hydroxypentanoic acid (HPA)(aka hydroxyvaleric acid). The pathway through angelicalactone was proposed by the Floridians [3], but no actual production of MTHF was reported. The hydrogenation path proceeding through HPA has been tested and the results reported in many publications with various final products indicated.

The dehydration of levulinic acid to angelicalactone is easily accomplished by simple heating of levulinic acid to about 160° C., acid promotes the dehydration, and distillation of the products at atmospheric or reduced pressure of about 10 to 50 mm Hg [3,5,6] (FIG. 1). Angelicalactone and water products separate in the collector. The resulting angelicalactone can be catalytically hydrogenated to 1,4-pentanediol (PDO) using barium-stabilized copper-chromite catalyst at 240° C. [6]. The PDO is readily converted to the MTHF by a dehydration reaction [7] (FIG. 2) owing to the thermal instability of the PDO. The acid-promoted reaction is accomplished in a similar manner to the formation of the angelicalactone from levulinic acid, i.e., by heating of the PDO in the presence of acid and the simple distillation of the MTHF product at 76°–80° C. A more recent version is the processing with Nafion®-H (Tradename of EI DuPont, Wilmington, Del.) resin in which a 90% yield was obtained within 5 hr at 135° C. [8].

Catalytic hydrogenation of levulinic acid has been reported to produce a number of different products dependent upon the catalyst and conditions. These differences result from the variations in processing severity and the resulting extent of progress down a sequential pathway shown in FIG. 3. Levulinic acid is reduced to HPA which readily dehydrates to γ-valerolactone (GVL). GVL is hydrogenated to 1,4-pentanediol (PDO) which dehydrates to MTHF. Side products include pentanoic (aka valeric) acid and 1-pentanol.

Early published results claim the recovery of HPA after reduction of levulinic acid with the catalyst sodium amalgam, nickel catalyzed hydrogenation in the vapor phase at 250° C. and electrocatalytically from an alkaline solution [10]. More recent studies claim the formation of the HPA product by hydrogenation using sodium metal in NaOH-ethanol solution at ambient conditions (60% yield after 4 hr) [10], or Raney nickel in aqueous alkali at 75° C. up to 250° C. with 2500 psig over pressure of hydrogen (84.1% yield after 27 min) [11], but in both cases the GVL product was recovered after dehydration of the HPA. A more recent study with Raney nickel at 10 to 90° C. in aqueous alkali without added hydrogen [12] showed a combined product of HPA and GVL at conversions of 53 to 65% after 1 hour.

Catalytic production of the GVL from levulinic acid has been investigated by several groups. Schutte and Thomas [13] developed an hydrogenation process using platinum oxide catalyst in an organic solution of the levulinic acid. They were concerned with decomposition of the GVL at higher temperatures (above 160° C.) [14] and questioned earlier reports of high temperature production [16]. Their studies showed a solvent effect on the room temperature reduction at 2–3 atm hydrogen over-pressure. A yield of 87% was achieved in ethyl ether after 44 hr of reaction. Reaction in acetic acid or ethanol proceeded more slowly with only 48% and 52% yield, respectively, after the 44 hr. These results compliment the work of Jacobs and Scott [15] who found that GVL was unreactive over platinum oxide in ethanol solution. Similar tests showed that AL was hydrogenated to GVL in this system.

A process for hydrogenation of levulinic acid was later patented wherein the catalysis is done in the neat liquid phase with a nickel catalyst at 900 psig hydrogen and 175°–200° C. [16]. The basis for the patent is found in a later article [4] where the results are given as 94% yield of GVL after 3 hr at 100° C. up to 220° C. and an initial hydrogen pressure of 700 psig with Raney nickel. Also reported in that article is the use of copper-chromite catalyst to produce a complex product of 11% GVL, 44% PDO and 22% of water solution possibly containing MTHF. The process was completed over a temperature range of 190° C. up to 300° C. over 80 min of reaction time. The reaction was performed in neat liquid phase at 267 atm pressure (200 atm hydrogen initial pressure). This is the first report of the MTHF byproduct, although its ready formation from PDO by thermal decomposition/dehydration [4] explains its presence. Christian et al. contrast their result with the earlier report [17] of direct reduction of the ketone functional group in GVL and other lactones to produce MTHF and related furans. Also reported is a second process using Raney nickel catalyst at less severe conditions (100 atm initial hydrogen pressure and 273° C. reaction temperature) which produced 62% GVL and 21% PDO.

Two later papers describe rhenium catalysts for hydrogenation of levulinic acid to GVL. Rhenium black produced by in-situ reduction from rhenium heptoxide was used to produce a 71% yield of GVL from neat levulinic acid after 18 hr at 106° C. and 150 atm pressure [18]. The balance of the product is described as polymeric esters. It is noted in the text that those hydrogenations run in anhydrous acids always resulted in some by-product ester formation; those run in water solvent gave markedly reduced ester formation, or in most cases no ester formation. In related experiments with acetic acid, the in-situ rhenium catalyst was found to be the only effective catalyst (at only 150° C.) with platinum oxide, copper-chromite and nickel all inactive at temperatures of 250°–300° C. Another form of rhenium, Re(IV) oxide hydrate generated from ammonium perrhenate by reduction with zinc in $H_2SO_4$, was also shown to have useful catalytic properties. Levulinic acid was converted 100% to GVL at 152° C. and 200 atm pressure after 12 hr [19].

Related literature of interest deals with the hydrogenation of GVL. Hydrogenation of GVL over copper-chromite catalyst was described at 250° C. and 200–300 atm pressure [20]. The yield was 78.5% PDO and 8.1% 1-pentanol. In a later study [4] using a copper-chromite catalyst, up to 83% yield of PDO was achieved at 240°–260° C. In tests at higher temperature, 270°–290° C., PDO yields dropped to 32%, and an undisclosed amount of MTHF was found in a low-boiling product fraction.

More recent studies have focused on homogeneous catalysis of the hydrogenation steps. Joó et al. describe both ruthenium [21] and rhodium [22] complexes which can hydrogenate levulinic acid at low temperature (60° C.) in aqueous solutions. However, no indication of products is given. A more interesting study has identified GVL as the product from levulinic acid when using ruthenium iodocarbonyl complexes [23]. These complexes converted 85–100% of the levulinic acid to GVL in 8 hr @ 150° C. Other results with ruthenium triphenylphosphine complexes also show activity for the hydrogenation of levulinic acid to GVL, up to 99% conversion and 86% yield after 24 hr @ 180° C. [24], but these function in toluene solution and are not stable in water.

Although the literature describes useful processes for conversion of levulinic acid to MTHF, the processes require multiple steps with different catalysts and disparate operating conditions. Homogeneous catalysis has also been reported, but economic processing is not likely for the usual reasons of precious metal catalyst regeneration and recovery.

None of the prior art processes produced MTHF in a concentration or yield greater than about 4.5 mol %. Accordingly, there is a need for a fuel or fuel component of MTHF having a concentration greater than 4.5 mol %.

Further, there is a need in the art for a simpler conversion of levulinic acid to MTHF.

BACKGROUND REFERENCES

1. Kitano, M., Tanimoto, F., Okabayashi, M. "Levulinic Acid, A New Chemical Raw Material—Its Chemistry and Use," *Chem. Econ. Eng. Rev.* 7(7) 25–29, 1975.
2. Leonard, R. H. "Levulinic Acid as a Basic Chemical Raw Material," *Ind. & Eng. Chem.* 48(8) 1331–1341, 1956.
3. Thomas, J. J., Barile, R. G. "Conversion of Cellulose Hydrolysis Products to Fuels and Chemical Feedstocks," in *Energy from Biomass and Wastes* VIII, pp.1461–1494, Institute of Gas Technology, Chicago, Ill., 1984.
4. Christian, R. V., Jr., Brown, H. D., Hixon, R. M. "Derivatives of γ-Valerolactone, 1,4-Pentanediol, and 1,4-Di-(-cyanoethoxy)-pentane," *Jour. Amer. Chem. Soc.* 69, 1961–1963, 1947.
5. Leonard, R. H. *Method of Converting Levulinic acid into Alpha Angelica Lactone.* U.S. Pat. No. 2,809,203, issued Oct. 8, 1957.
6. Helberger, Von J. H., Ulubay, S., Civelicoglu, H. "Simple Procedure for Preparing α-Angelicalactone and Hydrogenolysis of Oxygen Heterocycles," *Ann.* 561, 215–220, 1949.
7. Freer, Perkin, "The Synthetical Formation of Closed Carbon-Chains," *Jour. Chem. Soc.* 51, 836–837, 1887; Lipp, A. "About 1,4-Pentanediol and Its Anhydride (Methyltetrahydrofuran)," *Chemische Berichte* 22, 2567–2573, 1889.
8. Olah, G. A.; Fung, A. P.; Malhotra, R, "Synthetic Methods and Reactions; 99. Preparation of Cyclic Ethers over Superacidic Perfluorinated Resinsulfonic Acid (Nafion-H) Catalyst," *Synthesis*, 474–476, 1981.
9. Smith, K.; Beauvais, R.; Holman, R. W. "Selectivity versus Reactivity: The Safe, Efficient Metal Hydride Reduction of a Bifunctional Organic," *Jour. Chem. Educ.* 70(4) A94–A95, 1993.
10. Schutte, H. A.; Sah, P. P. T.; "Normal Valerolactone," *Jour. Amer. Chem. Soc.* 48, 3163–3165, 1926.
11. Allen, B. B.; Wyatt, B. W.; Henze, H. R. "The Catalytic Hydrogenation of Some Organic Acids in Alkaline Solution," *Jour. Amer. Chem. Soc.* 61, 843–846, 1939.
12. Cook, P. L. "The Reduction of Aldehydes and Ketones with Nickel-Aluminum Alloy in Aqueous Alkaline Solution," *Jour. Org. Chem.* 27, 3873–3875, 1962.
13. Schutte, H. A.; Thomas, R. W. "Normal Valerolactone. III. Its Preparation by the Catalytic Reduction of Levulinic Acid with Hydrogen in the Presence of Platinum Oxide," *Jour. Amer. Chem. Soc.* 52, 3010–3012, 1930.
14. Schutte, H. A.; Thomas, R. W. "Normal Valerolactone. II.," *Jour. Amer. Chem. Soc.* 52, 2028, 1930. Jacobs, W. A.; Scott, A. B. "The Hydrogenation of Unsaturated Lactones to Desoxy Acids," 48, 601–613, 1930.
16. Kyrides, L. P.; Groves, W.; Craver, J. K. *Process for the Production of Lactones.* U.S. Pat. No. 2,368,366, issued Jan. 30, 1945.
17. Adkins, H. *Reactions of Hydrogen with Organic Compounds over Copper-Chromium Oxide and Nickel Catalysts.* University of Wisconsin Press, Madison, Wis., 1937, pp. 77–78.
18. Broadbent, H. S.; Campbell, G. C.; Bartley, W. J.; Johnson, J. H. "Rhenium and Its Compounds as Hydrogenation Catalysts. III. Rhenium Heptoxide,"*Jour. Org. Chem.* 24, 1847–1854, 1959.
19. Broadbent, H. S.; Selin, T. G. "Rhenium Catalysts. VI. Rhenium (IV) Oxide Hydrate," *Jour. Org. Chem.* 28(9) 2343–2345, 1963.
20. Folkers, K.; Adkins, H. "The Catalytic Hydrogenation of Esters to Alcohols. II," *Jour. Amer. Chem. Soc.* 54, 1145–1154, 1932.
21. Joó, F.; Tóth, Z.; Beck, M. T. "Homogeneous Hydrogenation in Aqueous Solutions Catalyzed by Transition Metal Phosphine Complexes," *Inorg. Chim. Acta* 25, L61–L62, 1977.
22. Joó, F.; Somsák, L.; Beck, M. T. "Peculiar Kinetics of Hydrogenations Catalyzed by Chlorotris-(sulphonated Triphenylphosphine) rhodium (I) in Aqueous Solutions," *Jour. Mole. Catal.* 24, 71–75, 1984.
23. Bracca, G.; Raspolli-Galletti, A. M.; Sbrana, G. "Anionic Ruthenium Iodocarbonyl Complexes as Selective Dehydroxylation Catalysts in Aqueous Solution," *Jour. Organomet. Chem.* 417, 41–49, 1991.
24. Osakada, K.; Ikariya, T.; Yoshikawa, A. "Preparation and Properties of Hydride Triphenylphosphine Ruthenium Complexes with 3-Formyl (or Acyl) Propionate," *Jour. Organomet. Chem.* 231, 79–90, 1982.

SUMMARY OF THE INVENTION

The present invention is based upon the surprising discovery that a 5-carbon compound selected from the group of 4-oxopentanoic acid, at least one lactone of 4-oxopentanoic acid, and combinations thereof, may be hydrogenated with a bifunctional catalyst having a first functionality of hydrogenation and a second functionality of ring-opening and preserve the pendant methyl group. It is understood by those of skill in the art of catalysis that a catalyst functionality facilitates a reaction by enhancing reaction kinetics but is not itself a reactant. In addition, it is understood that a catalyst may have several functionalities and is selected so that the reaction(s) of interest is/are not inhibited, nor are any other desirable intermediate reactions substantially inhibited.

It was further unexpectedly discovered that the same conditions of bifunctional catalyst in the presence of hydrogen are useful for catalyzing the different intermediate reactions for example angelicalactone to gamma-valerolactone and gamma-valerolactone to 1,4-pentanediol. Finally, it was surprising that levulinic acid could be converted to MTHF with heating in the presence of the bifunctional catalyst and hydrogen in a single process vessel. It was further unexpected to realize a yield of MTHF greater than 4.5 mol %.

It is an object of the present invention to provide an organic chemical product having a concentration of MTHF at least about 25 mol %

It is an object of the present invention to provide a method of hydrogenating a 5-carbon compound with a bifunctional catalyst.

It is a further object of the present invention to provide a method of converting levulinic acid to 2-methyltetrahydrofuran within a single process vessel and with a single bifunctional catalyst.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

According to the present invention, a method of hydrogenating a 5-carbon compound has the steps of:
(a) selecting the 5-carbon compound from the group consisting of 4-oxopentanoic acid, at least one lactone of 4-oxopentanoic acid, and combinations thereof;
(b) heating the 5-carbon compound in the presence of a bifunctional catalyst having a first functionality of hydrogenation and a second functionality of ring-opening, and hydrogen for a predetermined time; and
(c) withdrawing a hydrogenated product selected from the group consisting of a saturated lactone, 1,4-pentanediol, 2-methyltetrahydrofuran, and combinations thereof.

When the hydrogenated product composition includes MTHF, preferably at least about 25 mol % MTHF, more preferably at least about 50 mol % MTHF, and most preferably greater than about 75 mol % MTHF up to and including 100 mol % MTHF. In addition to the MTHF, alcohols are present as well as a fraction of unreacted reactant or intermediate compounds. Alcohols that may be present include 1-pentanol (1–25 mol %), 2-pentanol (0.05–2 mol %) and 2-butanol (0.05–5 mol %). Unreacted reactant or intermediate compounds include GVL (0.1–60 mol %), and 1,4-pentanediol (0.01–20 mol %). The unreacted compounds may be removed in whole or in part via distillation of the lighter MTHF and alcohols leaving behind the heavier unreacted compounds. It is preferred to select operating conditions to minimize throughput of unreacted compounds. For example, a continuous flow process with feedstock in the neat condition, reaction pressure of about 1500 psig, temperature in excess of 200° C., results from about 0.11 mol % to 4 mol % unreacted compounds. However, any of the product compositions having MTHF greater than 25 mol % may be useful as a fuel or blended fuel component.

Figure 4:
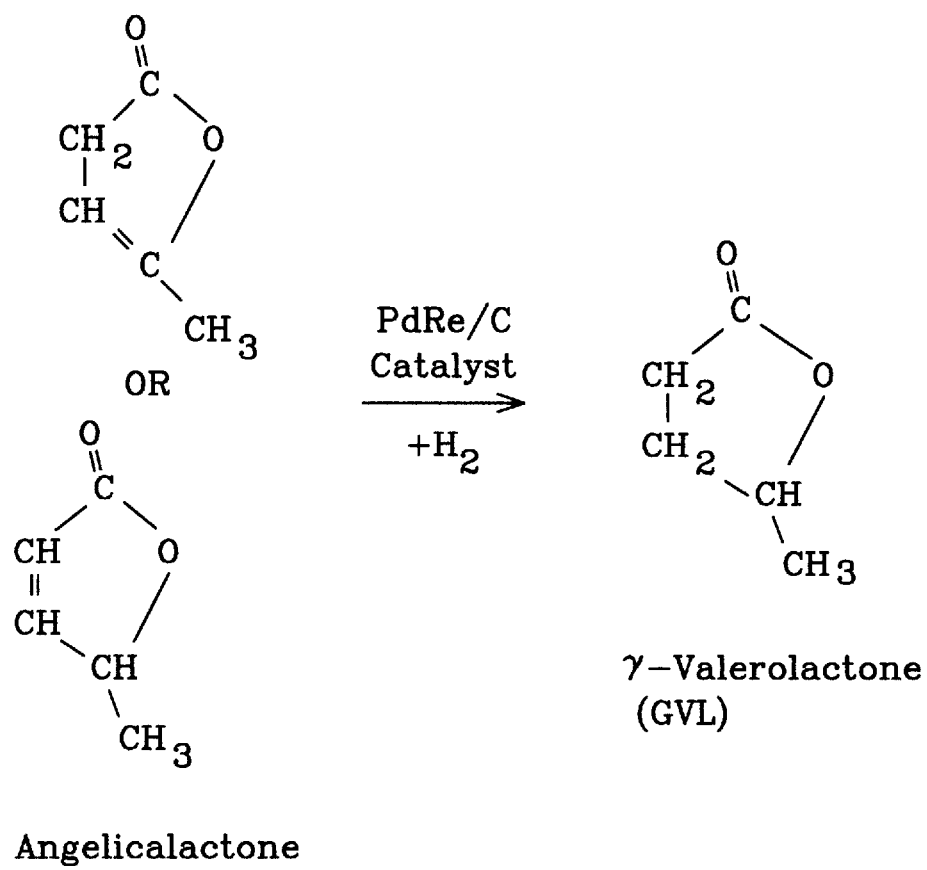
FIG. 4 is a reaction schematic according to the present invention of a catalyzed hydrogenation of angelicalactone to gamma-valerolactone.

Referring to FIG. 4, the method of the present invention is illustrated for the 5-carbon compound as angelicalactone and the hydrogenated product as gamma-valerolactone.

Figure 5:
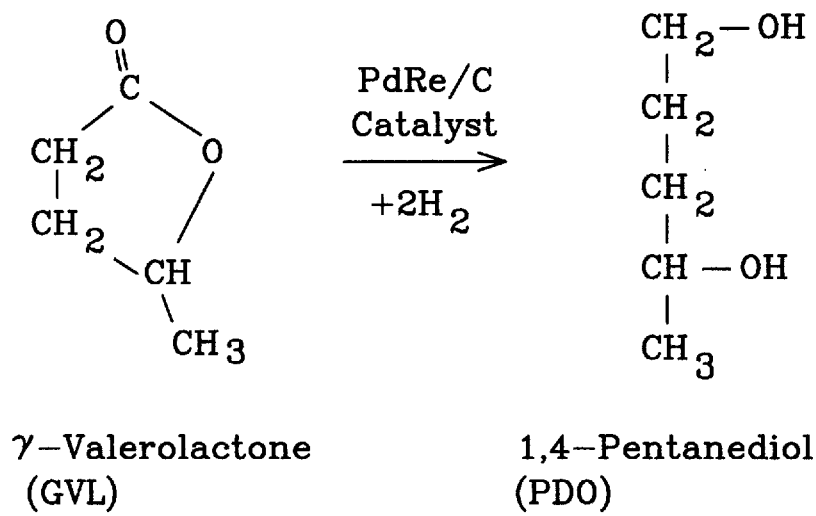
FIG. 5 is a reaction schematic according to the present invention of a catalyzed hydrogenation of gamma-valerolactone to 1,4-pentanediol.

Referring to FIG. 5, the method of the present invention is illustrated for the 5-carbon compound as gamma-valerolactone and the hydrogenated product as 1,4-pentanediol.

Figure 6:
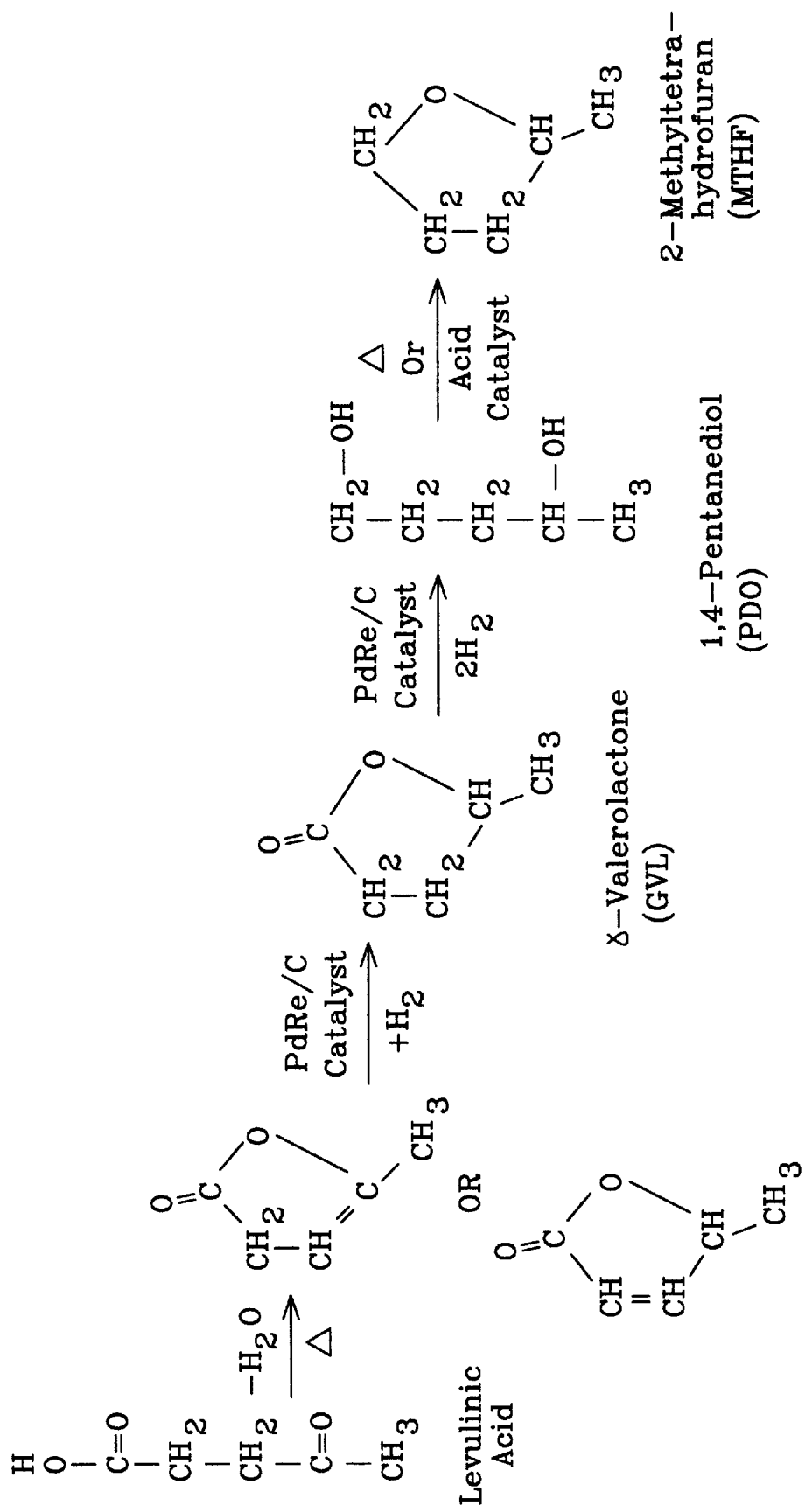
FIG. 6 is a reaction schematic according to the present invention of a complex conversion of levulinic acid to MTHF.

In FIG. 6, the method of the present invention is part of an overall process wherein the 5-carbon compound is levulinic acid dehydrated to angelicalactone, and the hydrogenated product is 2-methyltetrahydrofuran dehydrated from 1,4-pentanediol. The catalytic hydrogenations occur between the dehydrations.

The 5-carbon compound, 4-oxopentanoic acid is levulinic acid. Lactones of 4-oxopentanoic acid include but are not limited to two types of angelicalactone, gamma-valerolactone, and combinations thereof. Pentanediol specifically is 1,4-pentanediol.

The bifunctional catalyst is a metallic or bimetallic catalyst, preferably on a support. The first functionality of hydrogenation is provided by a first metal including but not limited to noble metal, copper, nickel, rhenium and combinations thereof. The first metal typically has a zero valence. The noble metal is selected from the group of noble metals including Group VIII for example palladium, platinum, rhodium ruthenium, osmium iridium, and combinations thereof. Preferred is palladium.

The second functionality of ring-opening is provided by a second metal. The second metal chemical name or symbol may be the same or different from that of the first metal. In the case of different metals, the catalyst is bimetallic. In either case, the second metal may have a positive valence greater than the valence of the first metal. The second metal of the bimetallic catalyst may be alloyed with the noble metal or placed separately on the catalyst support. It is preferred that the second metal be placed separately on the catalyst support. The second metal is selected from the group of rhenium, ruthenium, nickel, copper, nickel, tin, cobalt, manganese, iron, chromium, molybdenum, tungsten, and combinations thereof. Rhenium is preferred. The second metal may be in a zero valence or metallic state, or in a positive valence state, for example as an oxide (e.g. chromite) and/or as a salt.

The bifunctional catalyst may be used with reactions in the gas or liquid phase.

The support is a high surface area (at least about 50 $m^2/g$) metal oxide including but not limited to carbon, alumina, titania, zirconia, magnesium silicate and combinations thereof.

A preferred palladium-rhenium catalyst has from about 0.5 wt % to about 10 wt % palladium with about 5 wt % palladium preferred. The amount of rhenium may vary from about 1 wt % to about 12 wt %, with about 5 wt % preferred. The carrier material is preferably carbon, but may be any porous catalyst carrier material including but not limited to alumina, MgSiO, or other metal oxide. The catalyst may contain other metals beyond the noble metal and the second metal provided it does not substantially interfere with the activity of the noble metal/second metal combination.

With any bifunctional catalyst, operating temperature may range from about 100° C. to about 300° C.; and with the preferred palladium/rhenium on a carbon support catalyst, the operating temperature is preferably from about 200° C. to about 250° C., most preferably about 240° C. A hydrogen partial pressure is required for hydrogenation. Operating pressure includes hydrogen partial pressure reactant and product vapor pressure and impurity partial pressure. Operating pressure is preferably greater than about 10 atm, more preferably from about 50 atm to about 250 atm, further preferably from about 60 atm to about 140 atm, and most preferably about 100 atm. Operating temperature and/or pressure may vary when using different catalyst metal(s) and/or different support material.

Semi-Batch Reactor System Used For Examples

Figure 7:
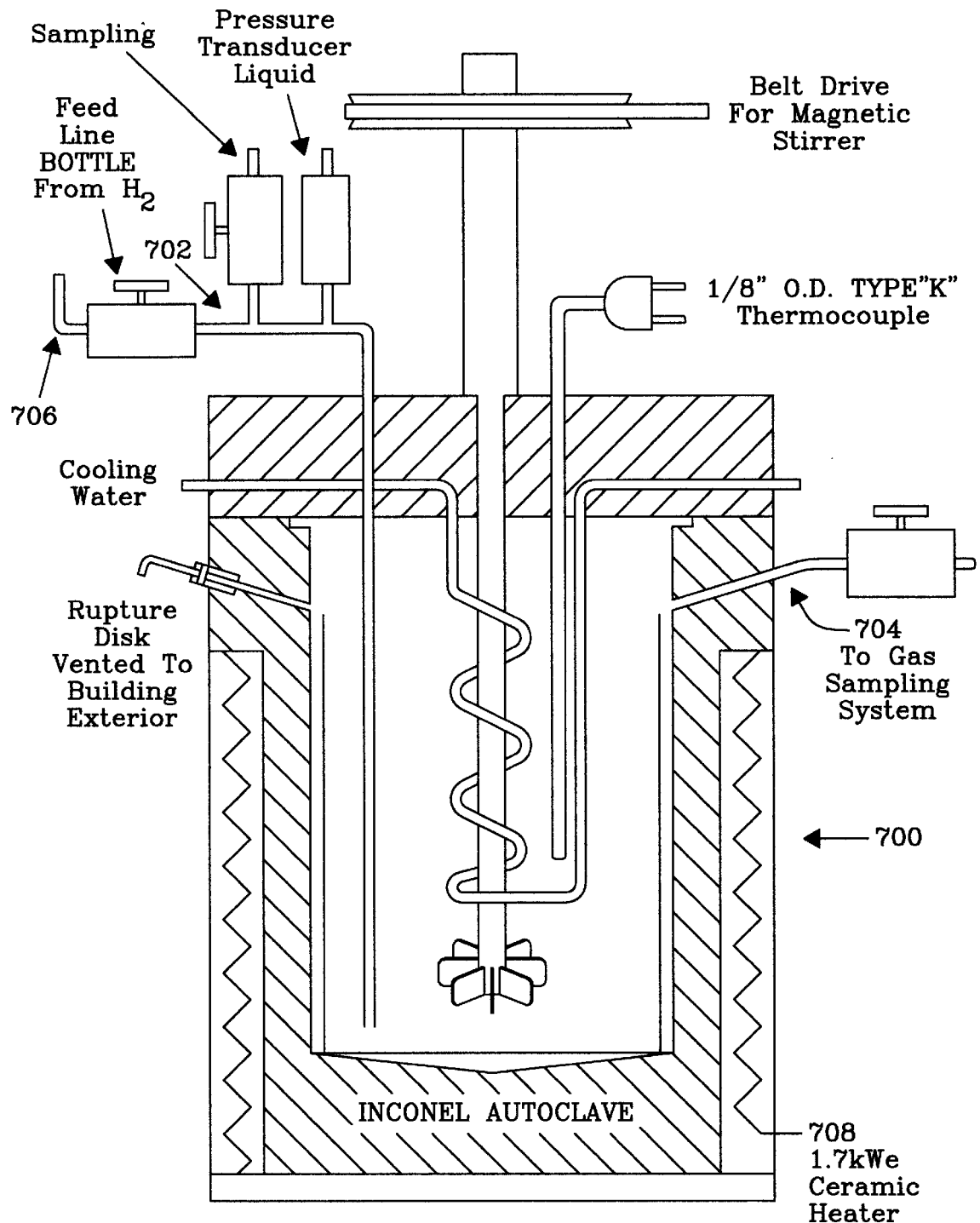
FIG. 7 is a cross section of a semi-batch reactor.

The reactor system used for examples 1–3 was a stirred, high-pressure autoclave shown in FIG. 7. The vessel 700 was modified with a sample ports, one liquid product sample port 702, and a gas sample port 704 permitting both liquid and gaseous products to be removed during the experiments while maintaining operating temperature and pressure. A hydrogen inlet port 706 allowed addition of hydrogen to the reactor to maintain a nearly constant reaction pressure. A ceramic heater 708 provided thermal energy to achieve elevated temperature within the vessel 700.

Operation of the semi-batch reactor involves adding an aliquot of feedstock to the reactor vessel with a catalyst, and the reactor vessel was sealed. An initial fill of hydrogen was added to the vessel and the reactor was heated to the desired reaction temperature. While maintaining the reaction temperature and pressure, samples were withdrawn at intervals over the duration of the experiment. Subsequently the reactor was cooled, depressurized to recover the residual gas product and opened to recover the residual liquid product.

The products were analyzed by gas chromatographic methods. The products and feedstocks were separated reasonably well for quantitation at the ±/10% level. Gas chromatography-Mass spectrometry was used to verify the identities of the various peaks while reagent grade standards were used for comparison of retention times and for calibration of the response factors of the various components of interest.

EXAMPLE 1

Using the semi-batch reactor, a 10% levulinic acid solution in water with catalyst was sealed inside the reactor. An initial fill of hydrogen was added to the reactor and it was heated to the desired reaction temperature of 200° C. or 250° C. at an operating pressure of 100 atm. Samples were withdrawn at intervals over a 6-hr experiment.

Nickel catalysts gave poor yields of the MTHF product while high conversions of the levulinic acid occurred. Temperatures used were sufficiently high that the levulinic acid would likely undergo dehydration to the angelicalactone (AL), but this intermediate was apparently quickly hydrogenated to GVL since the AL was not detected in the product mix. The use of water as the reaction medium apparently inhibited the formation of MTHF by driving the equilibrium of the 1,4-pentanediol (PDO) dehydration reaction away from the MTHF product. 2-Butanol (BuOH) was identified as the major liquid-phase byproduct in these tests. Results of product analyses are given in Table 1.

TABLE 1

| Levulinic Acid Hydrogenation Results in Water with Various Nickel Catalysts | | | | |
|---|---|---|---|---|
| | 5% Ni/ 5% Re 250° C. | 50% Ni 250° C. | 50% Ni/ 5% Re 250° C. | 50% Ni/ 7.5% Re 200° C. |
| LA conversion, % | 100 @ 30 min | 99 @ 30 min | 100 @ 0 min | 100 @ 0 min |
| Peak MTHF yield, mole % | 3 @ 6 hr | 7 @ 6 hr | 9 @ 4 hr | 15 @ 6 hr |
| Peak GVL/PDO yield, mole % | 79 @ 1 hr | 86 @ 1 hr | 98 @ 0 hr | 86 @ 0 hr |
| MTHF:2-butanol, mass ratio | 0.2 | 1.2 | 0.2 | 0.5 |
| Carbon gasification, % | 4.4 | 5.5 | 0.8 | 1.3 |

EXAMPLE 2

A second series of tests in the semi-batch reactor was done with a suite of catalysts using a feedstock of 10% levulinic acid in 1,4-dioxane solvent. Operating pressure was 100 atm.

The results of the dioxane tests are given in Tables 2a and 2b. The ruthenium on carbon catalyst shows high activity. At low temperature it was able to convert all of the levulinic acid readily to the GVL and PDO intermediates.

TABLE 2a

Levulinic Acid Hydrogenation Results in Dioxane with Various Catalysts

| Catalyst | 10% Ru on Carbon | 1% Ru/ 50% Ni on MgSiO | 7.5% Re/ 50% Ni on $Al_2O_3$ | 7.5% Re/ 50% Ni on $Al_2O_3$ repeat |
|---|---|---|---|---|
| Temperature (°C.) | 120 | 200 | 200 | 200 |
| LA conversion, % | 100 @ 0 min | 97 @ 30 min | 96 @ 0 min | 95 @ 0 min |
| Peak MTHF yield, mole % | 12 @ 6 hr | 30 @ 6 hr | 46 @ 5 hr | 28 @ 6 hr |
| Peak GVL/PDO yield, mole % | 99 @ 0 hr | 99 @ 1 hr | 74 @ 0 hr | 104 @ 1 hr |
| MTHF:2-BuOH, mass ratio | 1.3 | 1.7 | 6.0 | 2.9 |
| Carbon gasification, % | 0.1 | 28 | 4.9 | 3.6 |

TABLE 2b

Levulinic Acid Hydrogenation Results in Dioxane with Various Catalysts

| Catalyst | 7.5% Re/50% Ni on MgSiO | 7.5% Re/50% Ni on MgSiO | 2.5% Pd on carbon |
|---|---|---|---|
| Temperature (°C.) | 200 | 220 | 150 |
| LA conversion, % | 100 @ 0 min | 100 @ 0 min | 35 @ 6 hr |
| Peak MTHF yield, mole % | 45 @ 6 hr | 47 @ 6 hr | 0 @ 6 hr |
| Peak GVL/PDO yield, mole % | 103 @ 0 hr | 101 @ 0 hr | 35 @ 6 hr |
| MTHF:2-BuOH, mass ratio | 3.3 | 2.7 | 0 |
| Carbon gasification, % | 3.5 | 4.6 | 0 |

The MTHF yield was only marginal with a significant BuOH byproduct but little gas formation. Use of Ru promoted nickel catalyst at higher temperature gave good LA conversion with good MTHF yield. However, BuOH yield was still high and gas production was very high. Re promoted nickel gave a better MTHF yield with improved specificity versus BuOH. Levulinic acid conversion was very fast as was conversion of the GVL and PDO intermediates, shown in Tables 2a and 2b by the declining recovery already evident in the first sample. Gas production was significant but not nearly as high as with Ru promotion. A rerun of the alumina supported catalyst showed strong evidence of catalyst deactivation. The rate of GVL and PDO conversion was reduced as was the production of MTHF and gas. Specificity for MTHF also dropped. Re promoted nickel on magnesium silicate support showed similar high activity as with the alumina support, but the MgSiO support is expected to be more stable. A higher temperature test was done with the same catalyst showing somewhat improved activity but a loss of specificity for MTHF. The palladium catalyst tested showed low activity at the lower temperature tested. Limited levulinic acid conversion was achieved and no MTHF (nor BuOH nor gas) was formed.

EXAMPLE 3

Rhenium promoted palladium catalysts were substituted for the catalysts of Examples 1 and 2 and gave exceptional or unexpected results as shown in Table 3. These Re/Pd catalysts were all formulated on an 81% CTC carbon from Englehard Corp., Cleveland, Ohio. At lower temperature, the Re/Pd catalyst shows a slow rate of hydrogenation of levulinic acid and the GVL and PDO intermediates. The specificity for MTHF is high with no BuOH or gas byproducts. At the temperature of 200° C. the levulinic acid conversion is slow, but the improved yield of MTHF is still produced with high specificity. Even at the higher temperature where higher rates of hydrogenation are achieved, the specificity for MTHF is maintained (though somewhat less) with almost no gas production. The addition of more rhenium promoter caused a higher rate of hydrogenation of the levulinic acid, but the MTHF yield was improved only marginally. The MTHF specificity was maintained. Tests at higher and lower operating pressure were also performed showing an effect on the rate of levulinic acid conversion and conversion of the GVL and PDO intermediates to MTHF. There was no significant increase in gas production, nor clear effect on the selectivity for MTHF relative to 2-BuOH.

TABLE 3

Levulinic Acid Hydrogenation Results with Rhenium-Promoted Palladium Catalysts

| Catalyst | 5% Re/5% Pd | 5% Re/5% Pd | 5% Re/5% Pd | 10% Re/5% Pd | 10% Re/5% Pd | 10% Re/5% Pd |
|---|---|---|---|---|---|---|
| Temperature (°C.) | 150 | 200 | 250 | 200 | 200 | 200 |
| Pressure (psig) | 1500 | 1500 | 1500 | 1500 | 1000 | 2000 |
| LA conversion, % | 4 @ 0 min | 32 @ 0 min | 100 @ 0 min | 89 @ 0 min | 22 @ 0 min | 94 @ 0 min |
| Peak MTHF yield, mole % | 18 @ 6 hr | 34 @ 6 hr | 66 @ 6 hr | 38 @ 6 hr | 41 @ 6 hr | 48 @ 6 hr |
| Peak GVL/PDO yield, mole % | 112 @ 2 hr | 104 @ 1 hr | 84 @ 0 hr | 98 @ 30 min | 125 @ 60 min | 101 @ 0 min |
| MTHF:2-BuOH, mass ratio | no BuOH | 22 | 13 | 22 | 37 | 32 |
| Carbon gasification, % | no methane | 0.1 | 0.1 | 0.1 | no methane | 0.1 |

The same batch of catalyst was used in all three 5% Re/5% Pd tests and the same batch of catalyst was used in all three 10% Re/5% Pd tests. The catalyst was recovered by filtration, washed and vacuum dried between tests. It was not reduced between tests. There is no evidence from these tests of significant loss of catalyst activity during the period of the three tests. However, minor loss of activity could still be masked by the different temperatures used here.

EXAMPLE 4

Figure 8:
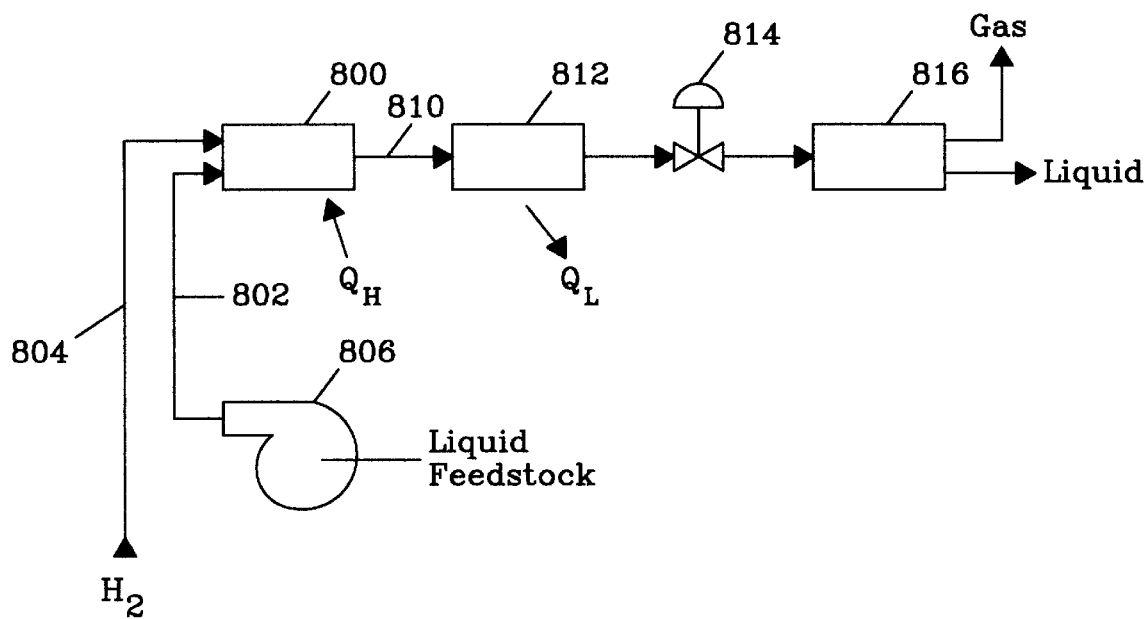
FIG. 8 is a schematic of a continuous flow reactor.

Experiments were conducted to demonstrate continuous flow operation of the present invention. The continuous flow reactor is shown in FIG. 8. A tubular reactor 800 had a liquid feedstock inlet 802 and a hydrogen inlet 804. Liquid feedstock was pressurized with a syringe pump 806. Heat $Q_H$ was added to the tubular reactor 800 with an oil jacket (not shown). Reaction products exited an outlet 810 into a cooler 812 that removed heat $Q_L$. Cooled reaction products were depressurized through a back pressure regulator 814 then separated in a gas-liquid separator 816.

All continuous flow experiments used levulinic acid with an H$_2$/levulinic acid ratio of 5.9, in the presence of a catalyst of 5% Pd–5% Re on a carbon support. All continuous flow experiments were conducted at an operating pressure of 100 atm (1500 psig). The levulinic acid was processed both in the neat condition and as mixed with dioxane. Operating conditions for each run are shown in Table 4a.

TABLE 4a

Operating Conditions for 5% Pd/5% Re/Carbon Catalyzed Continuous Flow Conversion of Levulinic Acid

| Run ID | Temp. (°C.) | LHSV | WHSV | Conc. (Vol %) |
|---|---|---|---|---|
| 6C | 242 | 0.75 | 16.9 | neat |
| 7B | 242 | 1.00 | 22.5 | neat |
| 7C | 242 | 1.00 | 22.5 | neat |
| 7A | 242 | 1.50 | 33.8 | neat |
| 6B | 221 | 0.75 | 16.9 | neat |
| 5A | 221 | 1.50 | 32.6 | 60 |
| 5C | 221 | 0.75 | 16.3 | 60 |
| 5B | 221 | 1.00 | 21.7 | 60 |
| 8A | 221 | 0.60 | 13.5 | neat |
| 8C | 221 | 1.00 | 22.5 | neat |
| 8D | 221 | 0.75 | 16.9 | neat |

Results are shown in Table 4b showing nearly complete conversion of levulinic acid and high conversion of the process intermediates GVL and PDO in all tests. The rate of reaction is noticeably higher at the higher temperature. The specificity for the desired product, MTHF is also quite good, throughout. It is somewhat higher at the lower temperature, 221° C., (85 to 90%) compared the higher temperature, 242° C. (around 80%). The specificity is also slightly better in the solvent (1,4-dioxane) as opposed to the result with the pure feedstock while the conversion rate of the intermediates is surprisingly similar.

TABLE 4b

Results of Continuous Flow Conversion of Levulinic Acid

| Run ID | Levulinic Acid Conversion | GVL/PD Conversion | MTHF Specificity | MTHF Molar Yield |
|---|---|---|---|---|
| 6C | 100.00 | 99.8 | 78.9 | 81.1 |
| 7B | 99.90 | 99.1 | 77.5 | 78 |
| 7C | 99.85 | 71.5 | 74.6 | 61.9 |
| 7A | 99.80 | 86.7 | 81.2 | 72.7 |
| 6B | 99.86 | 92.7 | 88.4 | 81.3 |
| 5A | 100.00 | 50.4 | 90.6 | 70.6 |
| 5C | 100.00 | 88.9 | 89.7 | 89.7 |
| 5B | 100.00 | 72.5 | 89.8 | 89.8 |
| 8A | 99.70 | 92.9 | 74.5 | 68.9 |
| 8C | 99.80 | 81.8 | 79.5 | 63.6 |
| 8D | 100.00 | 93.8 | 80.6 | 76.2 |

The effect of reduced pressure operation (test 7C compared to test 7B) is an unexpectedly severe reduction in conversion and reduced specificity as well. However, the effect of increased operating pressure (test 8D compared to test 6B) is only a slight increase in conversion with reduced specificity.

The range of product composition from the continuous flow reactor tests are shown in Table 4c.

TABLE 4c

Product Composition (mol %)

| Product Component | All Tests | Tests 6B, 6C |
|---|---|---|
| MTHF | 50–90 | 75–90 |
| 1-pentanol | 1–25 | 10–25 |
| 2-pentanol | 0.05–2 | 0.05–2 |
| 2-butanol | 0.05–5 | 0.05–5 |
| GVL | 0.1–30 | 0.1–3 |
| 1,4-pentanediol | 0.01–10 | 0.01–1 |

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of hydrogenating a 5-carbon compound, comprising the steps of:
   (a) selecting the 5-carbon compound from the group consisting of 4-oxopentanoic acid, at least one lactone of 4-oxopentanoic acid, and combinations thereof;
   (b) heating the 5-carbon compound in the presence of a bifunctional catalyst having a first function of hydrogenating and a second function of ring opening, and hydrogen for a predetermined time; and
   (c) withdrawing a hydrogenated product selected from the group consisting of a saturated lactone, 1,4-pentanediol, 2-methyltetrahydrofuran, and combinations thereof.

2. The method as recited in claim 1, wherein the 5-carbon compound is angelicalactone and the hydrogenated product is gamma-valerolactone.

3. The method as recited in claim 1, wherein the 5-carbon compound is gamma-valerolactone and the hydrogenated and ring-opened product is 1,4-pentanediol.

4. The method as recited in claim 1, wherein the 5-carbon compound is levulinic acid dehydrated to angelicalactone, and the hydrogenated product is 2-methyltetrahydrofuran dehydrated and ring-closed from 1,4-pentanediol.

5. The method as recited in claim 1, wherein the first functionality is provided by a first metal selected from the group consisting of noble metal, copper, nickel, rhenium, and combinations thereof.

6. The method as recited in claim 5, wherein the noble metal is selected from the group consisting of palladium, platinum, rhodium, ruthenium, osmium, iridium, and combinations thereof.

7. The method as recited in claim 5, wherein the second functionality is provided by a bimetallic catalyst having a second metal selected from the group consisting of rhenium, ruthenium, nickel, copper, tin, cobalt, manganese, iron, chromium, molybdenum, tungsten and combinations thereof.

8. The method as recited in claim 7, wherein the second functionality is provided by a second metal with a positive valence.

9. The method as recited in claim 7 wherein the bimetallic catalyst has another metal.

10. The method as recited in claim 1, wherein said heating is done at a temperature of at least 100° C.

11. The method as recited in claim 10, wherein said temperature is from about 200° C. to about 250° C.

12. The method as recited in claim 11, wherein said temperature is about 240° C.

13. The method as recited in claim 1, wherein said first and second functionalities are provided by at least one metal on a support.

14. The method as recited in claim 13, wherein said support is selected from the group consisting of carbon, alumina, titania, zirconia, magnesium silicate and combinations thereof.

15. A method of making 2-methyltetrahydrofuran from levulinic acid, comprising the steps of:

(a) heating the levulinic acid in the presence of a bifunctional catalyst having a first functionality of hydrogenating and a second functionality of ring-opening, and hydrogen; wherein (b) the levulinic acid undergoes dehydration to angelicalactone which is catalytically hydrogenated to gamma-valerolactone which is further catalytically hydrogenated and ring-opened to 1,4-pentanediol which is finally dehydrated and ring-closed to 2-methyltetrahydrofuran; and (c) withdrawing the 2-methyltetrahydrofuran.

16. The method as recited in claim 15, wherein the first functionality is provided by a first metal selected from the group consisting of noble metal, copper, nickel, rhenium, and combinations thereof.

17. The method as recited in claim 16, wherein the noble metal is selected from the group consisting of palladium, platinum, rhodium, ruthenium, osmium, iridium, and combinations thereof.

18. The method as recited in claim 16, wherein the second functionality is provided by a bimetallic catalyst having a second metal selected from the group consisting of rhenium, ruthenium, nickel, copper, tin, cobalt, manganese, iron, chromium, molybdenum, tungsten and combinations thereof.

19. The method as recited in claim 18, wherein the second functionality is provided by a second metal with a positive valence.

20. The method as recited in claim 18 wherein the bimetallic catalyst has another metal.

21. The method as recited in claim 15, wherein said heating is done at a temperature of at least 100° C.

22. The method as recited in claim 21, wherein said temperature is from about 200° C. to about 250° C.

23. The method as recited in claim 22, wherein said temperature is about 240° C.

24. The method as recited in claim 15, wherein said noble metal and said second metal are on a support.

25. The method as recited in claim 24, wherein said support is selected from the group consisting of carbon, alumina, titania, zirconia, magnesium silicate and combinations thereof.

26. The method as recited in claim 1, wherein the 2-methyltetrahydrofuran comprises:

a yield of the 2-methyltetrahydrofuran greater than 4.5 mol %.

27. The method as recited in claim 1, wherein the hydrogenated product comprises:

2-methyltetrahydrofuran in combination with a concentration of alcohols from about 1 mol % to about 32 mol %.

28. The method as recited in claim 27, wherein said alcohols are selected from the group consisting of pentanol, butanol and combinations thereof.

29. The method as recited in claim 15, wherein the 2-methyltetrahydrofuran comprises:

a yield of the 2-methyltetrahydrofuran greater than 4.5 mol %.

30. The method as recited in claim 15, wherein the hydrogenated product comprises:

2-methyltetrahydrofuran in combination with an amount of alcohols from about 1 mol % to about 32 mol %.

31. The method as recited in claim 30, wherein said alcohols are selected from the group consisting of pentanol, butanol and combinations thereof.

32. An organic chemical product, comprising:

2-methyltetrahydrofuran in a concentration greater than 25 mol %; and alcohol in a concentration from about 1 mol % to about 32 mol %.

33. The organic chemical product as recited in claim 32, wherein said alcohol is selected from the group consisting of 1-pentanol, 2-pentanol, 2-butanol and combinations thereof.

34. The organic chemical product as recited in claim 33, further comprising an unreacted compound in an amount from about 0.1 mol % to about 80 mol %.

35. The organic chemical product as recited in claim 34 wherein said unreacted compound is selected from the group consisting of gamma-valerolactone, 1,4-pentanediol, and combinations thereof.

36. The organic chemical product as recited in claim 32 as a fuel or fuel component.

* * * * *

UNITED STATES PATENT AND TRADEMARK OFFICE
CERTIFICATE OF CORRECTION

PATENT NO. : 5,883,266
DATED : March 16, 1999
INVENTOR(S) : Elliott, et. al.

It is certified that error appears in the above-identified patent and that said Letters Patent is hereby corrected as shown below:

In Column 4, line 42, please add a return before the word "Jacobs, W.", and add "15." at the beginning of the new return.

Signed and Sealed this

First Day of May, 2001

Attest:

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 5,883,266
DATED : March 16, 1999
INVENTOR(S) : Elliott et al.

Figure 1:
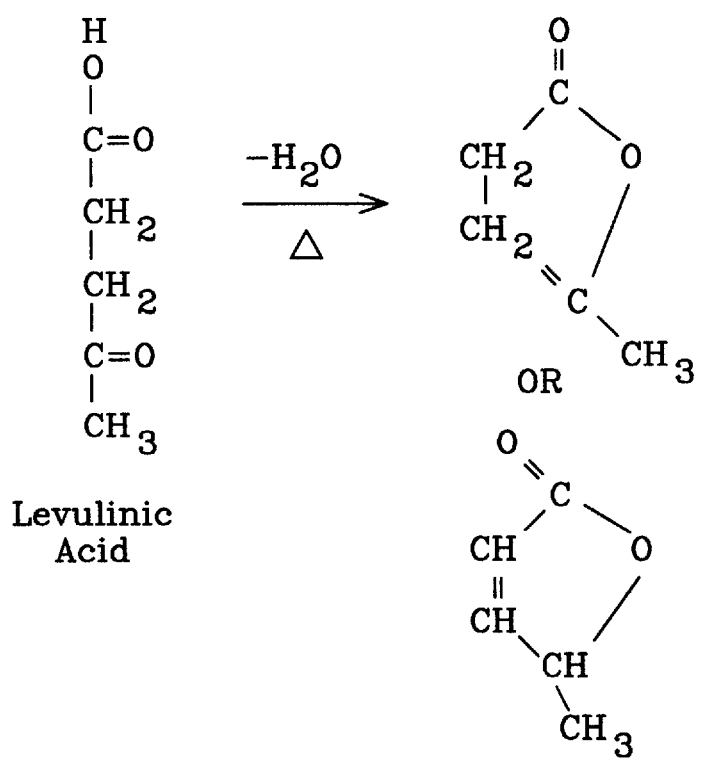
FIG. 1 is a reaction schematic of a prior art dehydration of levulinic acid to angelicalactone.
Figure 2:
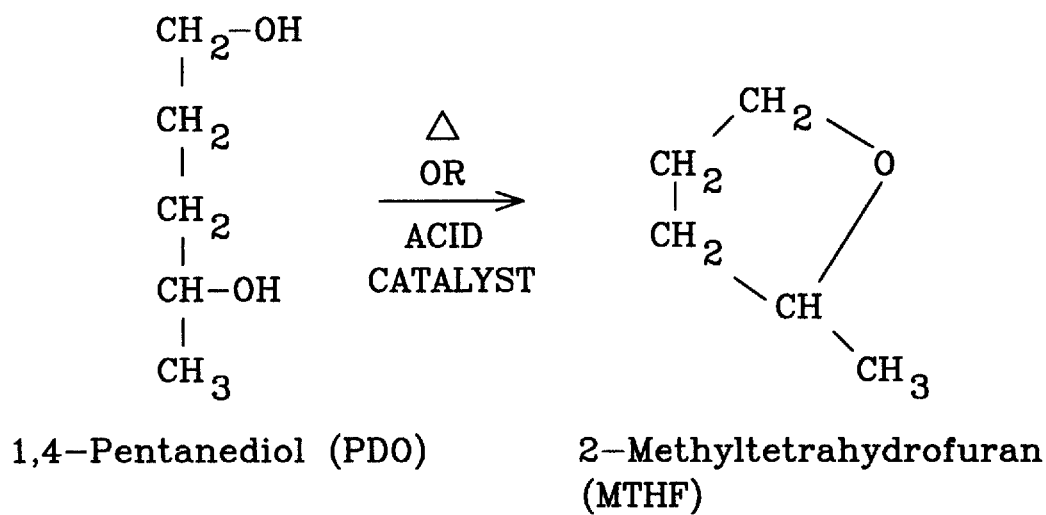
FIG. 2 is a reaction schematic of a prior art dehydration of 1,4-pentanediol to MTHF.
Figure 3:
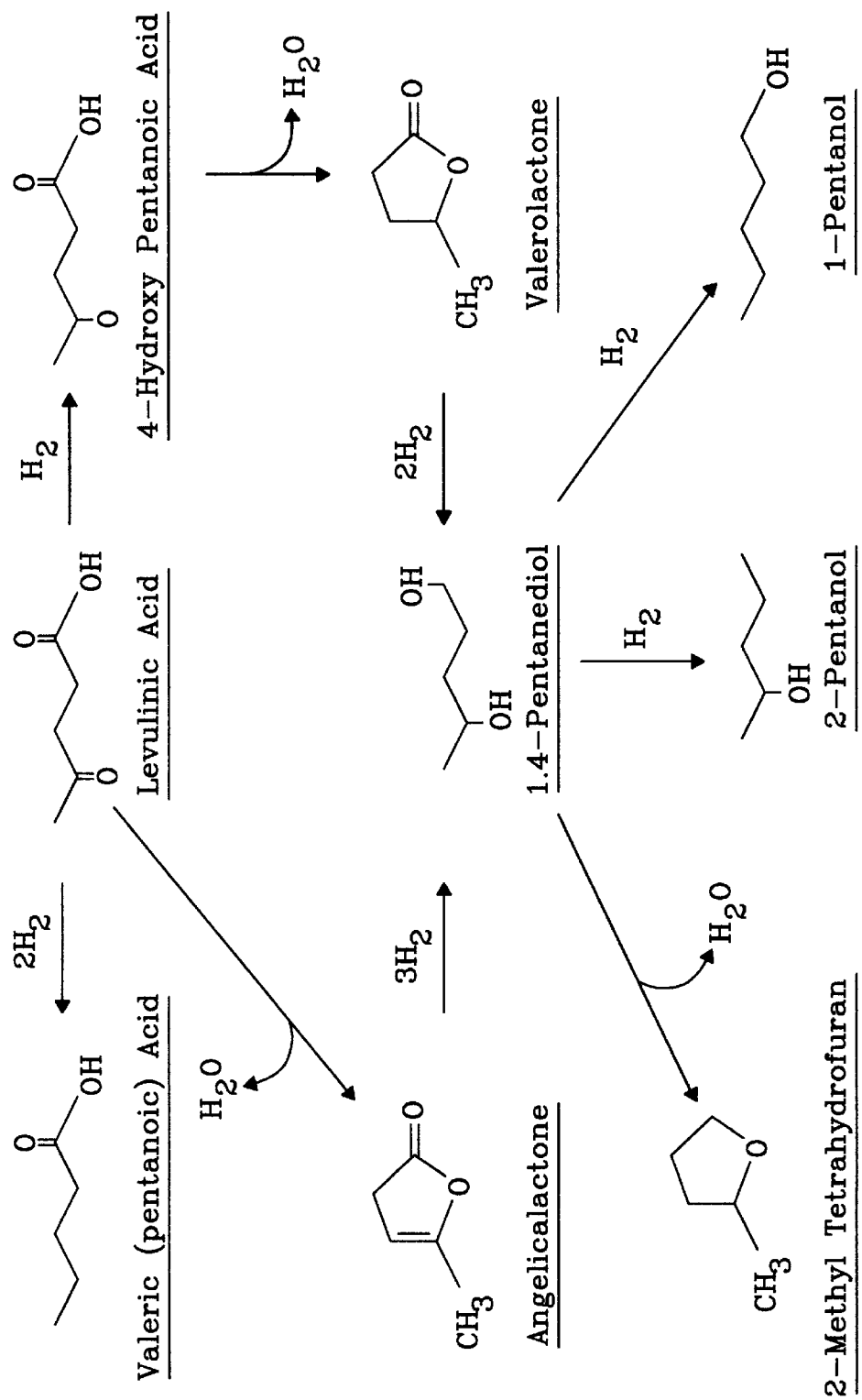
FIG. 3 is a reaction schematic for several pathways from levulinic acid to MTHF.

It is certified that error appears in the above-identified patent and that said Letters Patent is hereby corrected as shown below:

Figure 3,
Above 4-Hydroxy Pentanic Acid, please replace "O" with -- OH -- where "O" has a single bond to the carbon.

Signed and Sealed this

Eighteenth Day of September, 2001

Attest:

*Nicholas P. Godici*

NICHOLAS P. GODICI
*Attesting Officer*     *Acting Director of the United States Patent and Trademark Office*